US005888810A

United States Patent [19]

Meinersmann et al.

[11] Patent Number: 5,888,810
[45] Date of Patent: Mar. 30, 1999

[54] *CAMPYLOBACTERI JEJUNI* FLAGELLIN-*ESCHERICHIA COLI* LT-B FUSION PROTEIN

[75] Inventors: Richard J. Meinersmann, Lithonia, Ga.; Christian A. Khoury, Philadelphia, Pa.

[73] Assignee: The United States of America as represented by the Secretary of Agriculture, Washington, D.C.

[21] Appl. No.: 784,218

[22] Filed: Jan. 16, 1997

Related U.S. Application Data

[62] Division of Ser. No. 150,305, Nov. 12, 1993, abandoned.

[51] Int. Cl.$^6$ .................................................. C12N 15/31
[52] U.S. Cl. ...................... 435/320.1; 435/325; 435/693; 536/23.7
[58] Field of Search ................................ 435/320.1, 325, 435/69.3; 536/23.7

[56] References Cited

PUBLICATIONS

Khoury,C.A. "Isolation, Characterization, Sequencing, and Expression of the *Campylobacter jejeni*flagellar gene and assessment of the Expressed flagellar protein as a chicken vaccine". Ph.D. Thesis Athens, Georgia University of Georgia 1992.

Helmann, J.D., *Molec. Microbiol.*, vol. 5, pp. 2875–2882 (1991).
Khawaja et al, *Curr. Microbiol.*, vol. 24, pp. 213–221 (1992).
Fisher et al., *Molec. Microbiol.*,vol. 5, pp. 1151–1158 (1991).
Nuitjen et al., *J. Biochem. Chem.*, vol. 265, pp. 17798–17804 (1990).
Wang et al., *J. Bacteriol.*, vol. 172, pp. 949–955 (1990).
Labigne–Roussel et al., *J. Bacteriol.*, vol. 169, pp. 5320–5323 (1987).
Labigne–Roussel et al., *J. Bacteriol.*, vol. 170, pp. 1704–1708 (1988).
Clements, J.D., *Infect. Immun.*, vol. 58, pp. 1159–1166 (1990).
Jagusztyn–Krynicka et al., *Infec. Immun.*, vol 61, pp. 1004–1015 (1993).
Nakayama et al., *Biotechnology*, vol. 6, pp. 693–697 (1988).

*Primary Examiner*—Anthony C. Caputa
*Attorney, Agent, or Firm*—M. Howard Silverstein; John Fado; Janelle S. Graeter

[57] ABSTRACT

A fusion protein which comprises the B subunit of the labile toxin (LT-B) of *E. coli* and part of the flagellin (flaA) protein of *C. jejuni* is antigenic and is useful for decreasing colonization in chickens by *Campylobacter* species. The protein is produced by *E. coli* cells, transformed by the plasmid pBEB into which DNA sequences encoding the novel protein have been introduced.

2 Claims, 3 Drawing Sheets

```
TGA GCT GTT GAC AAT TAA TCA TCC GGC TCG TAT AAT GTG TGG AAT TGT GAA CGG ATA
ACA ATT TCA CAC AGG AAA CAG ACC ATG CCG GAA TTA GCT CCC CAG TCT ATT ACA GAA
CTA TGT TCG GAA TAT CGC AAC ACA CAA ATA TAT ACG AAG ATA CTA TCA
TAT ACG GAA TCG GCA GGC AAA AGA GAA ATG GTT ATC ATT ACA TTT AAG AGC GGC
GAA ACA TTT CAG GTC GAA GTC CCG AGT CAT CAA GAC TCC CAA AAA AAA GCC
ATT GAA AGG ATG AAG GAC ACA TTA AGA ATC ACA TAT CTG ACC GAG GCA ATT GAT
AAA TTA TGT GTA TGG AAT AAT AAA ACC CCC AAT GCG TCA ACA TCA GCA AGT ATG AAA
AAC TAC GCG CCG CAG GAT CCT GAA TTC CAA ATC GGC AGT GGT TCA ACA AGA TTT GAA ACC
AAA GCA ACT ATC GGT GCT CAA TCT ACT CAA ATC AAA GGT CTT ACT ATT AAA TAC AAT GGT
GGT GCT CAA AGT TTT ACT TCA GTT GAT AAT GTT GTG ATT TCA ACT GGA ACA GGA CTT
ATA GAA GAT TTT AAA GAT ATT GAG ATC GTT TCA ACT TCA GTT GGA ACA GGA CTT
GGA GCT TTG GCT GAA ACA GTA GGA ACT ATC AAT AGC GCT GAT ACA ACA GTT GCA ACT
TAC GAT GTA AAA ACT GGA GTA TAT GGT GTT TAT GCT ATA GAA GAC GGA TCT CAA GAC
TTT GCC ATT AAT ATT TCA GCT ATC AAT GCG GTT AAT ATT GAA GAC ACC GGA GAT GGT AAC
GGC TCT TTG ATT TCA GCT GGC AAG CTT GTT CTT ACA TCG AAT GAT GCT AAA ATA GCT
AAA GAT GAA AAC GGC AAG CTT GGT ATT GAT CTT TCT ATT TTG ACA AAA GAA AAC TAT GGG
ACT GGA GAT ATA GGT GTT AAA AAT GAT GGT CAA AAT ATA GGA AGT AGT ACC AAT CTT
CGA TTA TCT TTA GTT ACA ATT TCA GCA GAT ATT TCT AGA ATG TCA GTG TCT TTA AGA
AGT GCT ATA GGT ATG AAA GGT GTT ACA ACA GCC AAT GCC GAT GCT CAA ATT AAT TAT
GAA TCA AAA CAA AAG AAA TTT CAA ACG GAA TTC TCC GAT GAT TTC GGA TTT GGA TCT
AAA GGT GGA AAA TTT GTT TCC GAA TTC GCT GAT GCG CGT ACG TAA
```

FIG. 3

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 80 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Escherichia coli ( x i ) SEQUENCE DESCRIPTION: SEQ ID NO:1:

AACTACGCGC CGCAGGATCC TGAATTCGCT AATGATCCGA CGCGTGCACT GTAACTAGCT   60

GCAGCCAAGC TCCCAAGCTT   80

( 2 ) INFORMATION FOR SEQ ID NO:2:

( i ) SEQUENCE CHARACTERISTICS:
        ( A ) LENGTH: 80 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO:2:

AAGCTTGGGA GCTTGGCTGC AGCTAGTTAC AGTGCACGCG TCGGATCATT AGCGAATTCA   60

GGATCCTGCG GCGCGTAGTT   80

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GATCCTGAAT TCGCTAAT   18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GATCATTAGC GAATTCAG   18

( 2 ) INFORMATION FOR SEQ ID NO:5:

( i ) SEQUENCE CHARACTERISTICS:
        ( A ) LENGTH: 1197 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Campylobacter jejuni/Escherichia coli (ix) FEATURE:
    (A) NAME/KEY: CDS
    (B) LOCATION: 82..1197

(xi) SEQUENCE DESCRIPTION: SEQ ID NO:5:

```
TGAGCTGTTG ACAATTAATC ATCCGGCTCG TATAATGTGT GGAATTGTGA ACGGATAACA                60

ATTTCACACA GGAAACAGAC C ATG CCG GAA TTA GCT CCC CAG TCT ATT ACA                 111
                        Met Pro Glu Leu Ala Pro Gln Ser Ile Thr
                         1               5                  10

GAA CTA TGT TCG GAA TAT CGC AAC ACA CAA ATA TAT ACG ATA AAT GAC                  159
Glu Leu Cys Ser Glu Tyr Arg Asn Thr Gln Ile Tyr Thr Ile Asn Asp
             15                  20                  25

AAG ATA CTA TCA TAT ACG GAA TCG ATG GCA GGC AAA AGA GAA ATG GTT                  207
Lys Ile Leu Ser Tyr Thr Glu Ser Met Ala Gly Lys Arg Glu Met Val
         30                  35                  40

ATC ATT ACA TTT AAG AGC GGC GAA ACA TTT CAG GTC GAA GTC CCG GGC                  255
Ile Ile Thr Phe Lys Ser Gly Glu Thr Phe Gln Val Glu Val Pro Gly
     45                  50                  55

AGT CAA CAT ATA GAC TCC CAA AAA AAA GCC ATT GAA AGG ATG AAG GAC                  303
Ser Gln His Ile Asp Ser Gln Lys Lys Ala Ile Glu Arg Met Lys Asp
 60                  65                  70

ACA TTA AGA ATC ACA TAT CTG ACC GAG ACC AAA ATT GAT AAA TTA TGT                  351
Thr Leu Arg Ile Thr Tyr Leu Thr Glu Thr Lys Ile Asp Lys Leu Cys
 75                  80                  85                  90

GTA TGG AAT AAT AAA ACC CCC AAT TCA ATT GCG GCA ATC AGT ATG AAA                  399
Val Trp Asn Asn Lys Thr Pro Asn Ser Ile Ala Ala Ile Ser Met Lys
                 95                 100                 105

AAC TAC GCG CCG CAG GAT CCT GAA TTC CAA ATC GGC GCA AGT TCA AAC                  447
Asn Tyr Ala Pro Gln Asp Pro Glu Phe Gln Ile Gly Ala Ser Ser Asn
             110                 115                 120

CAA ACT GTG AAA GCA ACT ATC GGT GCT ACT CAA TCT TCT AAA ATC GGT                  495
Gln Thr Val Lys Ala Thr Ile Gly Ala Thr Gln Ser Ser Lys Ile Gly
         125                 130                 135

GTT ACA AGA TTT GAA ACC GGT GCT CAA AGT TTT ACT TCA GGT GTG GTT                  543
Val Thr Arg Phe Glu Thr Gly Ala Gln Ser Phe Thr Ser Gly Val Val
     140                 145                 150

GGT CTT ACT ATT AAA AAC TAC AAT GGT ATA GAA GAT TTT AAA TTT GAT                  591
Gly Leu Thr Ile Lys Asn Tyr Asn Gly Ile Glu Asp Phe Lys Phe Asp
155                 160                 165                 170

AAT GTT GTG ATT TCA ACT TCA GTT GGA ACA GGA CTT GGA GCT TTG GCT                  639
Asn Val Val Ile Ser Thr Ser Val Gly Thr Gly Leu Gly Ala Leu Ala
                 175                 180                 185

GAA GAG ATC AAT AAA AGC GCT GAT AAA ACA GGA GTT CGC GCA ACT TAC                  687
Glu Glu Ile Asn Lys Ser Ala Asp Lys Thr Gly Val Arg Ala Thr Tyr
             190                 195                 200

GAT GTA AAA ACA ACT GGC GTT TAT GCT ATA AAA GAA GGA ACT ACT TCT                  735
Asp Val Lys Thr Thr Gly Val Tyr Ala Ile Lys Glu Gly Thr Thr Ser
         205                 210                 215

CAA GAC TTT GCC ATT AAT GGA GTA ACT ATA GGA AAA ATT GAA TAC AAA                  783
Gln Asp Phe Ala Ile Asn Gly Val Thr Ile Gly Lys Ile Glu Tyr Lys
     220                 225                 230

GAC GGA GAT GGT AAC GGC TCT TTG ATT TCA GCT ATC AAT GCG GTT AAA                  831
```

| | | | | | | | | | | | | | | | |
|---|---|---|---|---|---|---|---|---|---|---|---|---|---|---|---|
| Asp | Gly | Asp | Gly | Asn | Gly | Ser | Leu | Ile | Ser | Ala | Ile | Asn | Ala | Val | Lys |
| 235 | | | | 240 | | | | | 245 | | | | | 250 | |

| | | | | | | | | | | | | | | | |
|---|---|---|---|---|---|---|---|---|---|---|---|---|---|---|---|
| GAT | ACC | ACA | GGA | GTT | CAA | GCT | TCT | AAA | GAT | GAA | AAC | GGC | AAG | CTT | GTT | 879 |
| Asp | Thr | Thr | Gly | Val | Gln | Ala | Ser | Lys | Asp | Glu | Asn | Gly | Lys | Leu | Val |
| | | | | 255 | | | | | 260 | | | | | 265 | |

| | | | | | | | | | | | | | | | |
|---|---|---|---|---|---|---|---|---|---|---|---|---|---|---|---|
| CTT | ACA | TCG | GCT | GAT | GGC | AGG | GGT | ATT | AAA | ATT | ACT | GGA | GAT | ATA | GGT | 927 |
| Leu | Thr | Ser | Ala | Asp | Gly | Arg | Gly | Ile | Lys | Ile | Thr | Gly | Asp | Ile | Gly |
| | | | 270 | | | | | 275 | | | | | 280 | | |

| | | | | | | | | | | | | | | | |
|---|---|---|---|---|---|---|---|---|---|---|---|---|---|---|---|
| GTT | GGT | TCT | GGT | ATT | TTG | GCA | AAT | CAA | AAA | GAA | AAC | TAT | GGG | CGA | TTA | 975 |
| Val | Gly | Ser | Gly | Ile | Leu | Ala | Asn | Gln | Lys | Glu | Asn | Tyr | Gly | Arg | Leu |
| | | 285 | | | | | 290 | | | | | 295 | | | |

| | | | | | | | | | | | | | | | |
|---|---|---|---|---|---|---|---|---|---|---|---|---|---|---|---|
| TCT | TTA | GTT | AAA | AAT | GAT | GGT | AGA | GAT | ATC | AAT | ATA | AGT | GGA | ACC | AAT | 1023 |
| Ser | Leu | Val | Lys | Asn | Asp | Gly | Arg | Asp | Ile | Asn | Ile | Ser | Gly | Thr | Asn |
| 300 | | | | | 305 | | | | | 310 | | | | | |

| | | | | | | | | | | | | | | | |
|---|---|---|---|---|---|---|---|---|---|---|---|---|---|---|---|
| CTT | AGT | GCT | ATA | GGT | ATG | GGT | ACA | ACA | GAT | ATG | ATT | TCT | CAA | TCT | TCA | 1071 |
| Leu | Ser | Ala | Ile | Gly | Met | Gly | Thr | Thr | Asp | Met | Ile | Ser | Gln | Ser | Ser |
| 315 | | | | | 320 | | | | | 325 | | | | | 330 |

| | | | | | | | | | | | | | | | |
|---|---|---|---|---|---|---|---|---|---|---|---|---|---|---|---|
| GTG | TCT | TTA | AGA | GAA | TCA | AAA | GGT | CAA | ATT | TCA | GCA | ACC | AAT | GCC | GAT | 1119 |
| Val | Ser | Leu | Arg | Glu | Ser | Lys | Gly | Gln | Ile | Ser | Ala | Thr | Asn | Ala | Asp |
| | | | | 335 | | | | | 340 | | | | | 345 | |

| | | | | | | | | | | | | | | | |
|---|---|---|---|---|---|---|---|---|---|---|---|---|---|---|---|
| GCT | ATG | GGA | TTT | AAT | TCT | TAT | AAA | GGT | GGT | GGA | AAA | TTT | GTT | TCC | GAA | 1167 |
| Ala | Met | Gly | Phe | Asn | Ser | Tyr | Lys | Gly | Gly | Gly | Lys | Phe | Val | Ser | Glu |
| | | | 350 | | | | | 355 | | | | | 360 | | |

| | | | | | | | | |
|---|---|---|---|---|---|---|---|---|
| TTC | GCT | AAT | GAT | CCG | ACG | CGT | GCA | CTG | TAA | 1197 |
| Phe | Ala | Asn | Asp | Pro | Thr | Arg | Ala | Leu | |
| | | 365 | | | | | 370 | | |

( 2 ) INFORMATION FOR SEQ ID NO:6:

( i ) SEQUENCE CHARACTERISTICS:
        ( A ) LENGTH: 371 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Pro | Glu | Leu | Ala | Pro | Gln | Ser | Ile | Thr | Glu | Leu | Cys | Ser | Glu | Tyr |
| 1 | | | | 5 | | | | | 10 | | | | | 15 | |

| | | | | | | | | | | | | | | | |
|---|---|---|---|---|---|---|---|---|---|---|---|---|---|---|---|
| Arg | Asn | Thr | Gln | Ile | Tyr | Thr | Ile | Asn | Asp | Lys | Ile | Leu | Ser | Tyr | Thr |
| | | | 20 | | | | | 25 | | | | | 30 | | |

| | | | | | | | | | | | | | | | |
|---|---|---|---|---|---|---|---|---|---|---|---|---|---|---|---|
| Glu | Ser | Met | Ala | Gly | Lys | Arg | Glu | Met | Val | Ile | Ile | Thr | Phe | Lys | Ser |
| | | 35 | | | | | 40 | | | | | 45 | | | |

| | | | | | | | | | | | | | | | |
|---|---|---|---|---|---|---|---|---|---|---|---|---|---|---|---|
| Gly | Glu | Thr | Phe | Gln | Val | Glu | Val | Pro | Gly | Ser | Gln | His | Ile | Asp | Ser |
| | 50 | | | | | 55 | | | | | 60 | | | | |

| | | | | | | | | | | | | | | | |
|---|---|---|---|---|---|---|---|---|---|---|---|---|---|---|---|
| Gln | Lys | Lys | Ala | Ile | Glu | Arg | Met | Lys | Asp | Thr | Leu | Arg | Ile | Thr | Tyr |
| 65 | | | | | 70 | | | | | 75 | | | | | 80 |

| | | | | | | | | | | | | | | | |
|---|---|---|---|---|---|---|---|---|---|---|---|---|---|---|---|
| Leu | Thr | Glu | Thr | Lys | Ile | Asp | Lys | Leu | Cys | Val | Trp | Asn | Asn | Lys | Thr |
| | | | | 85 | | | | | 90 | | | | | 95 | |

| | | | | | | | | | | | | | | | |
|---|---|---|---|---|---|---|---|---|---|---|---|---|---|---|---|
| Pro | Asn | Ser | Ile | Ala | Ala | Ile | Ser | Met | Lys | Asn | Tyr | Ala | Pro | Gln | Asp |
| | | | 100 | | | | | 105 | | | | | 110 | | |

| | | | | | | | | | | | | | | | |
|---|---|---|---|---|---|---|---|---|---|---|---|---|---|---|---|
| Pro | Glu | Phe | Gln | Ile | Gly | Ala | Ser | Ser | Asn | Gln | Thr | Val | Lys | Ala | Thr |
| | | 115 | | | | | 120 | | | | | 125 | | | |

| | | | | | | | | | | | | | | | |
|---|---|---|---|---|---|---|---|---|---|---|---|---|---|---|---|
| Ile | Gly | Ala | Thr | Gln | Ser | Ser | Lys | Ile | Gly | Val | Thr | Arg | Phe | Glu | Thr |
| | 130 | | | | | 135 | | | | | 140 | | | | |

| | | | | | | | | | | | | | | | |
|---|---|---|---|---|---|---|---|---|---|---|---|---|---|---|---|
| Gly | Ala | Gln | Ser | Phe | Thr | Ser | Gly | Val | Val | Gly | Leu | Thr | Ile | Lys | Asn |
| 145 | | | | | 150 | | | | | 155 | | | | | 160 |

| | | | | | | | | | | | | | | | |
|---|---|---|---|---|---|---|---|---|---|---|---|---|---|---|---|
| Tyr | Asn | Gly | Ile | Glu | Asp | Phe | Lys | Phe | Asp | Asn | Val | Val | Ile | Ser | Thr |
| | | | | 165 | | | | | 170 | | | | | 175 | |

-continued

| | | | | | | | | | | | | | | |
|---|---|---|---|---|---|---|---|---|---|---|---|---|---|---|
| Ser | Val | Gly | Thr 180 | Gly | Leu | Gly | Ala | Leu 185 | Ala | Glu | Glu | Ile | Asn 190 | Lys | Ser |
| Ala | Asp | Lys 195 | Thr | Gly | Val | Arg | Ala 200 | Thr | Tyr | Asp | Val | Lys 205 | Thr | Thr | Gly |
| Val | Tyr 210 | Ala | Ile | Lys | Glu | Gly 215 | Thr | Thr | Ser | Gln | Asp 220 | Phe | Ala | Ile | Asn |
| Gly 225 | Val | Thr | Ile | Gly | Lys 230 | Ile | Glu | Tyr | Lys | Asp 235 | Gly | Asp | Gly | Asn | Gly 240 |
| Ser | Leu | Ile | Ser | Ala 245 | Ile | Asn | Ala | Val | Lys 250 | Asp | Thr | Thr | Gly | Val 255 | Gln |
| Ala | Ser | Lys | Asp 260 | Glu | Asn | Gly | Lys | Leu 265 | Val | Leu | Thr | Ser | Ala 270 | Asp | Gly |
| Arg | Gly | Ile 275 | Lys | Ile | Thr | Gly | Asp 280 | Ile | Gly | Val | Gly | Ser 285 | Gly | Ile | Leu |
| Ala | Asn 290 | Gln | Lys | Glu | Asn | Tyr 295 | Gly | Arg | Leu | Ser | Leu 300 | Val | Lys | Asn | Asp |
| Gly 305 | Arg | Asp | Ile | Asn | Ile 310 | Ser | Gly | Thr | Asn | Leu 315 | Ser | Ala | Ile | Gly | Met 320 |
| Gly | Thr | Thr | Asp | Met 325 | Ile | Ser | Gln | Ser | Ser 330 | Val | Ser | Leu | Arg | Glu 335 | Ser |
| Lys | Gly | Gln | Ile 340 | Ser | Ala | Thr | Asn | Ala 345 | Asp | Ala | Met | Gly | Phe 350 | Asn | Ser |
| Tyr | Lys | Gly 355 | Gly | Gly | Lys | Phe | Val 360 | Ser | Glu | Phe | Ala | Asn 365 | Asp | Pro | Thr |
| Arg | Ala | Leu 370 | | | | | | | | | | | | | |

CAMPYLOBACTERI JEJUNI FLAGELLIN-ESCHERICHIA COLI LT-B FUSION PROTEIN

This application is a division of application Ser. No. 08/150,305 filed Nov. 12, 1993, now abandoned.

BACKGROUND OF THE INVENTION

1. Field of the Invention

Approximately 3 billion chickens are raised in the United States every year, and virtually all are contaminated with Campylobacter jejuni (C. jejuni). Currently, there is no vaccine or any other method available to the poultry industry for the prevention of colonization, therefore there exists a need to develop a product which will provide protection from C. jejuni contamination. This invention relates to a novel fusion protein which, upon administration to a poultry population, will decrease the incidence of colonization by C. jejuni. The protein is relatively simple to produce and purify, and it is expressed in large quantities and can be used without further treatment (beyond purification) for vaccination.

2. Description of the Prior Art

In recent years, C. jejuni has been recognized as a major human enteropathogen and is the species implicated in more than 95% of the cases of campylobacteriosis in the United States (Karmali et al. 1983. J. Infect. Dis., vol. 147, pp. 243–246). C. jejuni has also been recognized as a common cause of gastroenteritis worldwide (Georges-Courbot et al. 1989. Res. Microbiol. vol. 140, pp. 292–296) with two-thirds of the reported cases found in the United States (Bokkenheuser and Sutter. 1981. pp.301–310. In Diagnostic Procedures for Bacterial, Mycotic and Parasitic Infections. Ed. Balows and Hausler. 6th edition, American Public Health Association, Washington, D.C.). Several reports indicate that C. jejuni enteritis is associated with eating in restaurants (Genigeorgis, C. 1987. pp. 111–145. In Elimination of Pathogenic Organisms from Meat and Poultry. Ed. F. J. M. Smulders, Elsevier, Amsterdam), drinking raw milk or unchlorinated water (Hutchinson et al. J. Hyg. Cam., vol. 94, pp. 204–215; Schmid et al. 1987. J. Infect. Dis., vol, 156, pp. 218–222), eating under-cooked poultry meat (Harris et al. 1986. Am. J. Pub. Health, vol. 76, pp. 407–411; Izat and Gardner. 1986. Poultry Science, vol. 67, pp. 1431–1435), and living in a household with pets (Genigeorgis, supra; Vandenberghe et al. 1982. Br. Vet. J., vol. 138, pp. 356–361). C. jejuni is common in the intestine of most domestic and many wild animals and is present in high numbers in most birds (Bokkenheuser, supra).

Species of Camplyobacter enter into a non-pathological, commensal relationship in the intestine of the chicken (Juven et al. 1991. Eur. J. Clin. Microbiol., v. 70, pp. 95–103). Chickens carry the organism as part of the indigenous intestinal flora, and for this reason they have been suspected as an important vehicle in the transmission or Campylobacter spp. to humans (Izat and Gardner, supra; Juven et al., supra). Poultry has been implicated as the major reservoir of human campylobacteriosis in the developed world (Genigeorgis, supra). As many as 90% of broiler chickens may harbor this organism (Lam et al. 1992. Av. Dis., v. 36, pp. 359–363). The pathogen can survive the chicken processing procedures and may be present on the product in retail outlets (Hood et al. 1988. Epidem. Inf., vol. 100, pp. 17–25). In a study at a live poultry market in New York City, more than 80% of broiler chickens sold yielded the organism. In another study, 68% of the retail broiler carcasses tested had C. jejuni (Izat et al., supra). Undercooked or improperly handled poultry has been implicated in 50 to 70% of Campylobacter spp. infections in humans (Hood et al., supra). In a study on university students in Georgia infected with Campylobacter, 70% of the cases were accounted for by eating chicken, often undercooked or raw, and 30% by contact with cats [Tauxe et al. 1988. CDC Surveillance Summaries, vol. 37(SS-2), pp. 1–13].

In a five year study conducted by the CDC between 1982 and 1986, 41,343 isolates of Campylobacter were reported. This yielded an annual isolation rate of 5.5 per 100,000 persons (Tauxe et al., supra). C. jejuni represented 99% of the reported species.

Campylobacter is believed to establish itself in the host by reaching and colonizing the mucosal surface of the intestinal tract. Enteropathogenic bacteria must overcome a number of host defense mechanisms to establish infection or to colonize. As part of the host defense mechanism, the mucous layer quickly eliminates unattached organisms from the gastrointestinal tract. As a virulence factor, the motility of the bacterium allows it to traverse the mucous layer and attach to or invade the epithelial cells of the intestinal tract (Newell and McBride. 1985. J. Hyg. Camb., vol. 95, pp. 217–227). Motility and chemotaxicity are considered important factors in the mechanism of association of C. jejuni with the intestinal epithelium (Griffiths and Park. 1990. J. Appl. Bacteriol., vol. 69, pp. 281–301). Field et al. (1981. Infect. Immun., vol. 33, pp. 884–892) showed, by scanning electron microscopy, that C. jejuni were present on, in, and below the mucous gel in the lower ileum of infected neonatal mice 2 h after inoculation. The ability to swim through environments of high viscosity, such as mucous, depends on the possession of a specialized type of motility.

To establish the role of flagella in the virulence of C. jejuni, Newell and McBride (supra) used a wild type strain and two non-motile variants (one flagellate and one non-flagellate) to conduct some colonization experiments. Their results showed that the aflagellate variant colonized the intestinal tract poorly. This occurred because the organisms were rapidly eliminated from the gut. The nonmotile flagellate colonized the gut as successfully as the wild type strain in some cases. These results suggest that flagella, active or inactive, are necessary for the efficient colonization of the gastrointestinal tract.

In a similar study (Morooka et al. 1985. J. Gen. Microbiol., vol. 131, pp. 1973–1980), the colonization of the intestinal tract by several mutant strains differed strikingly according to their motility. The wild type strain colonized well, while the aflagellated mutants where cleared. A poorly motile mutant, which had short flagellar filaments, colonized mice better than the non-motile flagellated mutants. These observations confirmed Newell's conclusion, but further suggested that motility was a necessary factor for the intestinal colonization by this pathogen.

Bacterial colonization of mucosal surfaces depends on the bacteria being able to maintain close proximity to the mucosa and to attach so as to avoid being swept away (Griffiths and Park, supra). C. jejuni colonizes the small intestine, mainly the ileum (Griffiths and Park, supra), but it may also colonize the colon. Invasiveness, enterotoxin, and cytotoxin production have all been implicated in causing campylobacteriosis (Genigeorgis, supra).

During infection, antibodies are made to a variety of Campylobacter surface structures, e.g. outer membrane proteins, and lipopolysaccharides (McSweegan et al. 1987. Infect. Immun., vol. 55, pp. 1431–1435). Nachamkin and Hart (1985. J. Clin Microbiol, vol. 21, pp. 33–38) did some Western blot analysis of the human antibody response to *C. jejuni* cellular antigens during gastrointestinal infections. They used acute and convalescent phase sera from patients, and they analyzed the antibody activity against their homologous infecting strains and heterologous clinical isolates. Their results showed that with acute phase sera, 3 major bands were recognized, one of which corresponded to the flagellar antigen. Convalescent phase sera recognized many more proteins and the Campylobacter flagellin was the major immunodominant component in all sera tested. The flagellin was not the major protein however in Coomassie blue stained gels.

Winsor et al. (1985. *Gastroenterology*, vol. 90, pp. 1217–1222) carried on some experiments to determine which *C. jejuni* outer membrane antigens elicited secretory IgA (sIgA) by using Western blot analyses of fecal extracts in patients with naturally acquired campylobacteriosis. Seven out of the eight patients elicited sIgA titres. The antigen to which the immunoglobulin reacted very strongly was the 63 kd flagellar antigen.

The flagellum is a major antigen of the Campylobacter cell (Harris et al. 1987. *Am. J. Pub. Health,* vol. 76, pp. 407–411), and it is the immunodominant antigen recognized during an infection in humans (Pavloskis et al. 1991. *Infect. Immun.,* vol. 59, pp. 1159–1164). It has been reported that there were various classes of antibodies against the flagellar protein in convalescent sera (Ueki et al. 1988. *Microbiol. Immunol.,* vol. 32, pp. 327–337). Herbrink et al. (1988. *Eur. J. Clin. Microbiol. Infect. Dis.,* vol. 7, pp. 388–393) investigated the IgG, IgA, and IgM immune response against *C. jejuni* at various timepoints during and after infection in humans. Their results showed that IgG antibody titers generally remained at a constant level for more than 50 days, where IgA and IgM titers declined more rapidly to normal values within 30 to 50 days after onset of clinical symptoms.

When an isogenic aflagellar mutant was used to challenge a rabbit, the campylobacters were cleared in less than 24 h. There was no significant IgA response, and the non-flagellar mutant did not protect the rabbit against challenge with the parent strain (Pavloskis et al., supra).

Flagellar filament seems to carry some of the serogroup-specific epitopes, since non-flagellated mutants lose their capacity to be serotyped by the Lior procedure. For most LIO serogroups however, the contribution of the flagellum to serotypic specificity has yet to be determined (Harris et al., *J. Bacteriol.,* supra). Flagella are the locomotory organelles of bacteria (Power et al. 1992. *J. Bacteriol.,* vol. 174, pp. 3874–3883). They are reversible rotary devices, driven by protonmotive force that propel the bacteria through liquid environments (Macnab et al. 1991. *Trends in Genetics,* vol. 7, pp. 196–200). At a gross level, the known features of the flagellar apparatus are a filament, a hook, and a basal body. This structure is called the "filament hook basal-body complex" (Macnab and De Rosier. 1988. *Can. J. Microbiol.,* vol. 34, pp. 442–451). The locations of the flagellar components fall into five compartments: the cytoplasmic face of the cell membrane, the cell membrane itself, the periplasmic space, the outer membrane, and the cell exterior. The hook is attached to the basal body. The hook and filament are both external to the cell. The flagellar filament is the portion that performs the hydrodynamic work on the cell's environment.

A flagellar filament is a long helical thread of uniform thickness. Its thickness is around 20 nm and its length is 15 μm. Heating of flagellar filaments at 56° C. for 15 min disintegrated them and released a single protein called flagellin (Iino, T. 1985. In *Molecular Cytology of Escherichia coli,* Academic Press, London, pp. 9–37). The MW of the flagellin monomer differs among different bacterial species, ranging from 40,000 to 63,000. *C. jejuni* flagellin monomer has a MW of 63,000 (Ueki et al. 1987. *Microb. Immunol.,* vol. 31, pp. 1161–1171). The flagellin monomers, which formed globular units, are lined in 11 longitudinal rows, alternate with each other in adjacent rows, and form as a whole a tubular structure. Flagellin monomers at high concentration assemble by themselves and form filaments in vitro. The reaction is reversible, and the binding among the monomers is thought to be hydrophobic (Iino, supra).

The flagellar systems of similar bacteria, i.e. *Escherichia coli (E. coli)* and *Salmonella typhimurium (S. typhimurium),* are encoded by at least 40 genes organized into three regions on the chromosome (Mcnab, 1991, supra; Muller et al. 1992. *J. Bacteriol.,* vol. 174, pp. 2298–2304). However, more than 60 genes are known to be involved in motility and chemotaxis (Macnab, R. M. 1987. In *Escherichia coli* and *Salmonella typhimurium Cellular and Molecular Biology,* Vol. 1., Eds. Neidhardt et al. American Society for Microbiology, Washington, D.C., pp. 732–759). The genes associated with the motile behavior are divided into three groups (Macnab, 1991, supra). Genes whose products are essential for the assembly of the flagella are given the symbol 'fla'. Genes whose products are not necessary for the flagellar assembly, but essential for motor rotation, are given the symbol 'mot'. The group of genes whose products are responsible for chemotactic responsiveness and control of switching between clockwise and anticlockwise direction of rotation, are given the symbol 'che'. Nearly all of the flagellar, motility and chemotaxis genes are located in four clusters on the *E. coli.* chromosome (Macnab, 1991, supra).

The genes are organized into a number of operons, so regulation is especially critical with regards to the flagellin structural gene (Macnab and Aizawa. 1984. *Ann. Rev. Biophys. Bioeng.,* vol. 13, pp. 51–83). A flagellar filament of typical length contains about 20,000 subunits. Synthesis of proteins in such large quantities is very wasteful if the bacterium cannot incorporate the proteins into the flagellum, due to a basal body defect for example. The majority of the regulatory mechanisms operate at the transcriptional level (Macnab, 1991, supra). They regulate expression of the flagellar genes in a hierarchy that parallels their roles in the assembly pathway. Operons coding for proteins needed in the initial steps of the assembly, i.e. switch, basal body, and export apparatus components, are expressed early. Genes for filament structure, motor rotation and chemotactic signaling, whose products are needed only when the basal body-hook complex is complete, are expressed late. All of the early genes must be expressed to obtain transcription of the late genes. A functional defect in any of the early genes can prevent expression of the late genes (Macnab 1991, supra).

The alteration of the transcriptional specificity of the RNA polymerase by the synthesis of alternative sigma factors provides a powerful way of controlling gene expression (Helmann, J. D. 1991. *Molec. Microbiol.,* vol. 5, pp. 2875–2882). The flagellin protein accounts for greater than 98% of the mass of the bacterial flagellum. *C. jejuni,* among other enteric bacteria, was found to have a sigma-28-like promoter element preceding the flagellin genes (Helmann, supra). Another alternative sigma factor (sigma-54) was found to control flagellin expression in some bacteria. Campylobacters have two flagellin genes, flaA and flaB. A sigma-54-like promoter element was found upstream of the flaB gene, although only the sigma-28-dependent flaA protein is required for motility (Galan et al. 1990. *Gene,* vol. 94, pp. 29–35). The sigma factor is part of the control mechanisms over flagellin expression, the other mechanisms are still unknown.

The flagellin antigen is highly immunogenic (Khawaja et al. 1992. *Curr. Microbiol.*, vol. 24, pp. 213–221). The flaA flagellin protein has been divided into three distinct regions consisting of two common and one variable regions (Fisher and Nachamkin. 1991. *Molec. Microbiol.*, vol. 5, pp. 1151–1158). The two common regions, C1 and C2, comprising the N-terminal 170 amino acids and C-terminal 100 amino acids, showed 94% and 96% identity to *Campylobactyer coli* (*C. coli*) common flagellin regions, respectively. The variable V1 region, comprising the middle of the protein, shows 61% identity to *C. coli* residues. Comparison of these regions with the sequence of other bacteria, *E. coil* and Salmonella, showed a similar pattern but with much less identity.

The amino acid sequence of the flagellin N-terminal region, mainly the first 20 residues, has been shown to be homologous in all *C. jejuni* strains tested to date (Fisher and Nachamkin, supra). This part of the flagellin is essential for filament assembly. During assembly of the flagellum, flagellin subunits are transported through the center of the filament and polymerize at its tip (Nuitjen et al. 1990. *J. Biochem. Chem.*, vol. 265, pp. 17798–17804). Both termini of the flagellum are important to the extension of the filament, and the amino terminus is necessary for the transport. By deletion analysis (Logan et al. 1989. *J. Bacteriol.*, vol. 171, pp. 3031–3038), it was shown that the smallest *E. coli* flagellin capable of forming flagellar filament required the N-terminal 193 residues and the C-terminal 117 residues. The exposed antigenic regions are less restricted and susceptible to mutations, some of which are advantageous to the organism (Khawaja et al., supra).

Two copies of the flagellin gene of *C. jejuni* have been identified which are 95% identical (King et al. 1991. *Microb. Ecol. Health Dis.*, vol. 4, pp. 135–140). Flagellar expression is subject to both phase and antigenic variation in Campylobacter species (Logan et al., supra), probably as an adaptation to the environment and the immune response of the host (Nuitjen et al. 1991. *Infect. Immun.*, vol. 59, pp. 1100–1105). Phase variation refers to the ability of some strains to exhibit a bidirectional transition between flagellated and nonflagellated states (Guerry et al. 1990. *J. Bacteriol.*, vol. 172, pp. 1853–1860). Antigenic variation refers to the ability of some strains to synthesize alternate flagellin protein that are distinguishable antigenically and that have different molecular weights. The immunogenicity and antigenic diversity of campylobacter flagella makes them important antigens in serotyping schemes based on the heat-labile antigens like the Lior scheme (Logan et al. 1987. *J. Bacteriol.*, vol. 169, pp. 5072–5077). In some of the LIO serotypes the use of nonflagellated organisms has shown that the flagella can carry the serotype specific determinant (Logan et al., 1987, supra).

The two flagellin genes of *C. jejuni* 81116 were identified, cloned, and sequenced (Nuitjen et al., 1990, supra). The two copies of the flagellin genes were called flaA and flaB. Both genes are 1,731 base pairs each, they occurred as tandem repeats, and were 95% identical. They have the same orientation, and they are separated by a 173-bp intergenic region. The calculated moledular weights of flagellin A and B were 59,538 and 59,909, respectively. The estimated weight from polyacrylamide gels is 62,000; this difference is probably due to post translational modifications.

Nuitjen et al. (1990, supra) used two specific oligonucleotide probes to discriminate between the mRNA of flagellin A and B. In motile bacteria only mRNA transcribed from flagellin A was detected as a monocistronic messenger of about 1800 nucleotides. By carrying out primer extension studies on the mRNA, they located the start of transcription 43 nucleotides upstream of the ATG start codon. *C. coli* (Guerry et al. 1991. *J. Bacteriol.*, vol. 173, pp. 4757–4764) also have two copies of the fla gene, flaA and flaB. The two genes share 91.9% sequence identity. Both products are expressed and are required for a fully active flagella (Wassenaar et al. 1991. *EMBO J.*, vol. 10, pp. 2055–2061).

Harris et al. (1987, supra) showed that the flagella of certain strains of *C. jejuni* and *C. coli* undergo antigenic variation. *C. jejuni* 81116 expressed one of two flagellin proteins, one with a MW of 61,500 and the other with a MW of 60,000. A reversible DNA rearrangement has been detected in a *C. coli* strain, but not in *C. jejuni* (Harris, 1987, supra). King et al. (supra) studied the expression of flagellin with isolates associated with a milk-borne outbreak of campylobacteriosis. They found that the milk isolates expressed a flagellin with a MW of 62,000 while the human isolates expressed a 58,000 flagellin. They speculated that this antigenic variation gave a virulence advantage for the phenotype.

Very few *C. jejuni* genes have been cloned and expressed in *E. coli*. This is due mainly to the lack of genetic markers, the absence of a developed natural gene transfer mechanism, and possibly due to some distinct differences in the regulatory sequences of these two bacteria (Chan et al. 1988. *Gene*, vol. 73, pp. 185–191). Two genes that have been expressed in *E. coli* are proB (gamma-glutamylkinase) and proA (gamma-glutamylphosphate-reductase). These genes were isolated by complementation of pro mutant *E. coli*. It is speculated that these genes were expressed only because the host cells were under pressure. Some of the genes identified in *C. jejuni* are glyA gene (serine hydroxymethyltransferase) (Chan and Bingham. 1990. *Gene*, vol. 101, pp. 51–58; Chan, 1988, supra), lysyl-tRNA sypthetase gene (Chan and Bingham. 1992. *J. Bacteriol.*, vol. 174, pp. 695–701), and the 5S, 16S and 23S ribosomal RNA (Ouellette et al. 1987. *Antimicrob. Agents Chemother.*, vol. 31, pp. 1021–1026).

Wang and Taylor (1990. *J. Bacteriol.*, vol. 172, pp. 949–955) reported that growing cells of *C. jejuni* and *C. coli* could be naturally transformed by naked DNA without the requirement for any special treatment. Maximum competence was found in early log phase of growth. The cells took up their own DNA much better than *E. coli* DNA.

Recently Labine-Roussel et al. (1987. *J. Bacteriol.*, vol. 169, pp. 5320–5323) constructed a shuttle cloning vector which can be mobilized from *E. coli* to *C. jejuni*, *C. coli*, and *Campylobacter fetus* (*C. fetus*). This vector was used to carry on gene disruption and replacement via homologous recombination (Labigne-Roussel et al. 1988. *J. Bacteriol.*, vol. 170, pp. 1704–1708).

The host responses to intestinal microbial infections involves a complex interplay of soluble factors or mediators, leukocytes, epithelial and endothelial cells of the gut-associated lymphoid tissue (GALT). The GALT is one component of the mucosa-associated lymphoid tissue (MAST), which also includes the bronchial, salivary, nasopharyngeal and genitourinary lymphoid tissues. The GALT consists of discrete lymphoid follicles scattered along the wall of the small intestine (Mesteky and McGhee. 1987. *Adv. Immunol.*, vol. 40, pp. 153–229).

The GALT in chickens consists of the bursa of Fabricius, cecal tonsils (CT), Peyer's patches (PP), and lymphocyte aggregates in the intraepithelium and in the lamina propria (LP) of the gastrointestinal wall. The bursa of Fabricius was considered to be the only site where antibody-forming cells could form (Befus et al. 1980. *J. Immunol.,* vol. 125, pp. 2626–2632). However, surgical ablation of the bursa of Fabricius, even in early embryonic development, does not completely inhibit the production of a humoral response. Thus, other non-bursal lymphoid tissue support some B cell differentiation (Befus et al., supra).

It has been suggested that prevention of infection by *C. jejuni* can be attained by blocking the colonization factor with specific antibodies (Ueki et al., supra). Wu et al. (1991. *Infect. Immun.,* vol. 59, pp. 2555–2559) showed that the flagellar protein was the major antigen recognized by intestinal lavage IgA in mice infected with *C. jejuni*.

Serum antibody response to invasive enteric pathogens is very important in protection against systemic infections. The initial immunologic response to enteric infection occurs at the level of the intestinal mucosa. Secretory immunoglobulin A (sIgA) response at the intestinal mucosa is a primary defense against enteric infections (Winsor et al. supra). Stern et al. (1990. *Avian Dis.,* vol. 34, pp. 595–601) found that specific anti-*C. jejuni* antibodies diminish the ability of the bacterium to colonize the gut of 1-day-old chicks when incubated with the organism as compared with preincubation with phosphate buffered saline.

The flagella of *C. jejuni* are essential in the colonization of the intestine. Nonflagellated organisms are quickly cleared from the intestine. Chicken polyclonal antiflagellin antibodies as well as monoclonal antiflagellin antibodies have been found to prevent *C. jejuni* from colonizing the chickens or to increase the dose of bacteria required to colonize the chickens (Carr, unpublished). Flagellar antigens are therefore potential candidates for vaccines as well as suitable antigens for diagnostic purposes, since the flagellin protein is immunodominant during human infections.

Kim et al. (1989. *Infect. Immun.,* vol. 57, pp. 2434–2440) immunized chickens with live *E. coli* expressing *Eimeria acervulina* merozoite recombinant antigen. The transformant cells were administered orally. Their results suggested that the recombinant vaccine could elicit antigen-specific humoral and cellular immune responses against the protozoan. Challenge with infective oocysts enhanced both immune responses, implying that the vaccine primed the chicken immune system against this protozoan. The protection, however, was partial. Immunoglobulin and T-cell responses against the recombinant antigen could be detected 7 days after vaccination.

Oral immunization to induce immunity against infectious diseases is convenient, relatively safe, and takes advantage of the mass of lymphoid tissue associated with the gut (Liang et al. 1988. *J. Immun.,* vol. 141, pp. 1495–1501).

The protective role of sIgA is well documented in many experimental models. sIgA neutralizes viruses, toxins, enzymes, inhibits adherence of bacteria to epithelial surfaces (Mesteky and McGhee, supra). sIgA binds to and agglutinates bacteria, but it is not thought to be bateriocidal (McSweegan et al., supra). Thus the induction of specific sIgA is desireable to selectively inhibit and clear colonizing bacteria from the gut. The presence of antibody-antigen complexes in the gut is known to stimulate the production of large quantities of mucus. This flow of mucus will trap the pathogens which will be more readily removed by normal intestinal peristalsis. Moreover, sIgA are better adapted in secretions, being more resistant to denaturation and proteolytic breakdown than IgG antibodies (Pierre et al. 1988. *Immunology,* vol. 18, pp. 51–56).

The major natural pathway for stimulating the immune system is thus through the GALT, where natural or artificially introduced antigens penetrate through the highly pinocytic and phagocytic M cells and interact with resident accessory and lymphoid cells (Mesteky and McGhee, supra). Precursor IgA B cells leave the site, mature and home back to the lamina propria of the GALT where they differentiate into IgA plasma cells specific for ingested antigens (Mesteky and McGhee, supra).

SUMMARY OF THE INVENTION

It is an object of the invention to provide a fusion protein which comprises the B subunit of the labile toxin, (LT-B) of *E. coli* and part of the flagellin (flaA) protein of *C. jejuni*.

It is another object of the invention to provide a plasmid comprising the DNA sequence which codes for the novel protein.

It is also an object of the invention to provide a culture of *E. coli* which has been transformed by the novel plasmid.

Other objects and advantages of the invention will become readily apparent from the following description.

BRIEF DESCRIPTION OF THE DRAWINGS

FIG. 3 is the DNA sequence of the LT-B/fla fusion gene (SEQ ID NO:5).

DETAILED DESCRIPTION OF THE INVENTION

Figure 1:
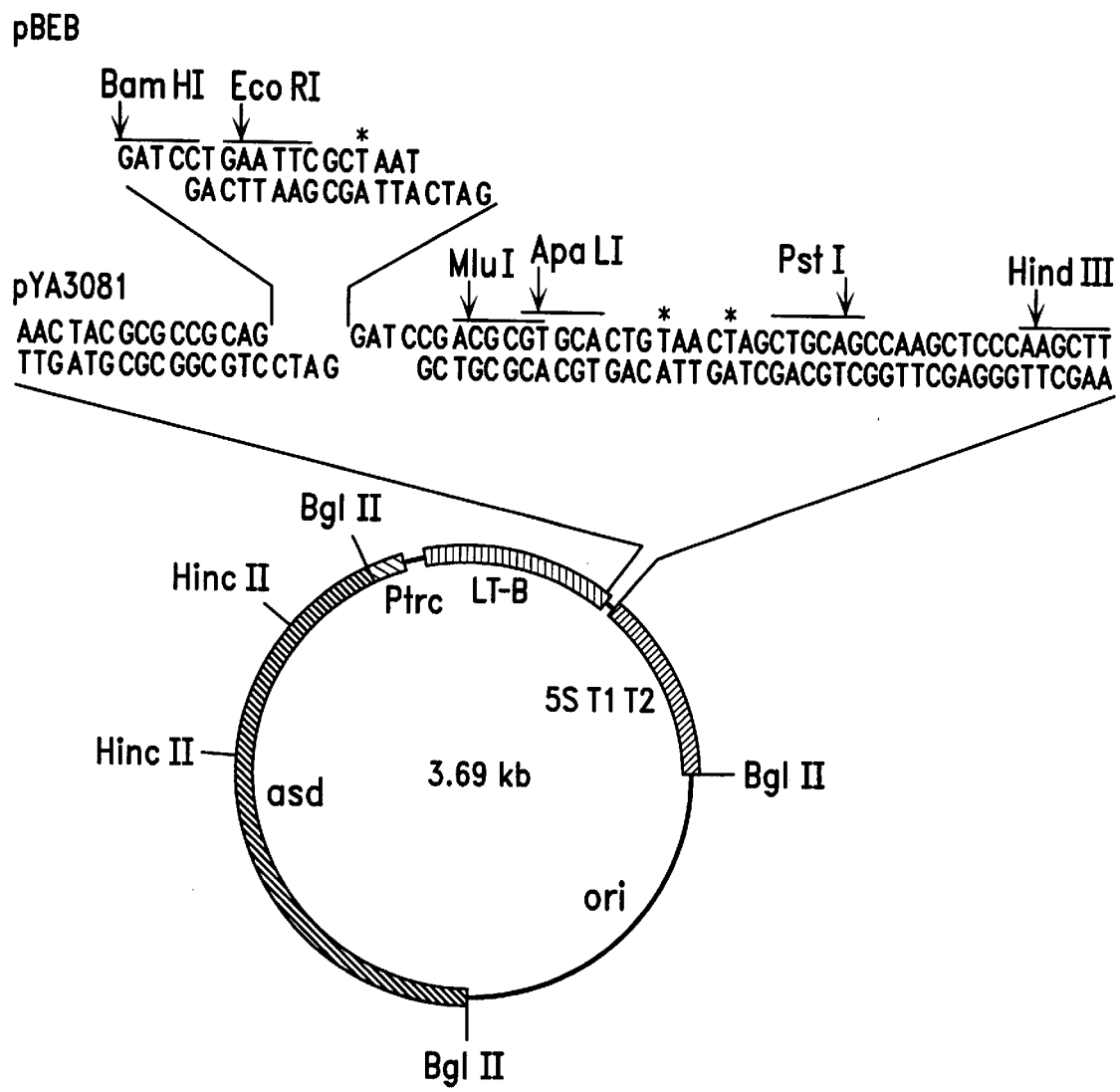
FIG. 1 is a map of pYA3081 (SEQ ID NO:1 and SEQ ID NO:2) showing the multiple cloning site and the adapter inserted to give pBEB. The asterisks(*) indicate the stop codons.
Figure 2:
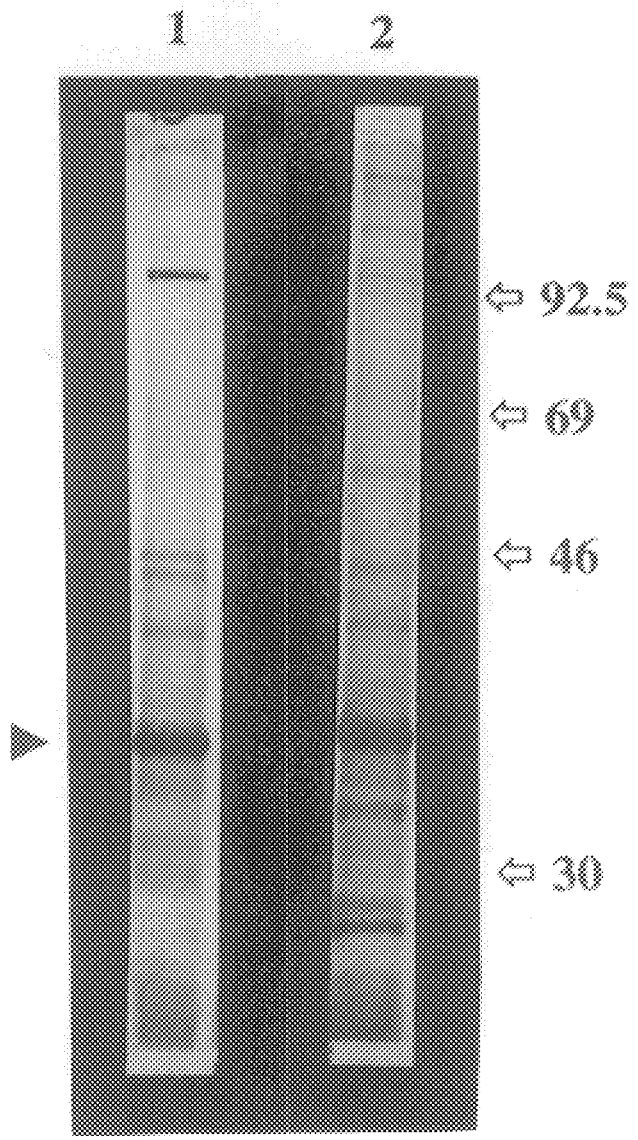
FIG. 2 is a photograph of a Western blot analysis of fusion protein extract. Lane 1 was developed with rabbit anti-LT serum, and Lane 2 was developed with chicken anti-flagellin serum. Markers on the right indicate the molecular weight in kilodaltons. Solid arrowhead on left indicates the fusion protein; this band was not present when extracts from pBEB transformed cells were analysed with anti-flagellin serum.

The novel protein is produced by a strain of *E. coil* as a result of transformation with a plasmid construct. The protein is composed of the LT-B toxin of *E. coli* and part of the flagellin (flaA) protein of *C. jejuni*. The LT-B protein is highly immunogenic, and it is known to bind to GM1 ganglioside found on the surface of all eukaryotic cells. Thus the LT-B portion of the protein was selected to deliver the flagellin antigen to the mucosal surfaces, thereby enhancing the immune system to mount a reaction against *C. jejuni* and thus diminishing colonization by that organism. In addition, the toxin from which it was derived was known to have an adjuvant effect on secretion of IgA when mixed with or bound to an antigen (Clements, J. D. 1990. *Infect. Immun.,* vol. 58, pp. 1159–1166; Elson, C. O. 1989. *Curr. Top. Microbiol. Immunol.,* vol. 146, pp. 29–33; Wilson et al. 1989. *Scand. J. Immunol.,* vol. 29, pp. 739–745), and the same effect was also demonstrated when antigens were produced as fusion proteins with the B-subunit (Clements, supra). Plasmids have been developed for the production of such fusion proteins.

Initially, efforts were made to construct a fusion protein composed of LT-B fused to a nearly complete flaA utilizing such a plasmid (pPX1604), which contains the gene coding for the intact full length B-subunit of LT following a lacZ promoter. The flaA gene was isolated by synthesizing two primers (fla1 and fla2) complementary to two DNA termini of the published flaA sequence (Nuitjen et al., 1990, supra, herein incorporated by reference). *C. jejuni* DNA was amplified by mixing with primers and performing a polymerase chain reaction. The two primers had NcoI restriction sites added to the 5' ends which were used to clone the flaA gene into the plasmid vector pPX1604. The 1.7 kb gene was isolated from a low melt agarose gel and cloned into the NcoI site in pPX1604 downstream from the *E. coil* LT-B subunit in an in-frame insertion, allowing the expression of a fusion protein. No expressed LT-B-flaA fusion protein could be detected, however.

Since a fusion protein containing the whole flaA gene could not be expressed, a lambda gt11 library was used to select a clone containing a 1.1 kb fragment of the flaA gene (truncated at both ends from the wild type flaA) downstream and in frame with the β-galactosidase gene.

A new plasmid was then constructed (as described by Khoury, C. A., published thesis, Nov. 14, 1992 and herein incorporated by reference) and designated pBEB (FIG. 1). The plasmid vector pYA3081 (described by Jagusztyn-Krynicka et al. 1993. *Infec. Immun.,* vol. 61, pp. 1004–1015, and herein incorporated by reference) was obtained from R. Curtiss III and modified in order to facilitate the insertion of the construct into the plasmid. This vector is 3.69 kb in length and was selected because it carries a multiple cloning site (MCS) with BamHI, MluI and ApaLI unique restriction sites at the downstream end, and it carries the LT-B gene without the signal sequence of the protein, which prevents the fusion protein from being secreted. In addition, pYA3081 has the asd gene from *S. typhimurium* and will complement asd mutant cells of *E. coil* and *S. typhimurium* (Nakayama et al. 1988. *Biotechnology,* vol. 6, pp. 693–697). In the absence of diamino palmetic acid (DAP), asd mutants undergo lysis. Since DAP is not present in vertebrate tissues, this balanced-lethal combination imposes the necessity for all living *E. coil* vaccine strains (asd mutant) to possess the plasmid in order to survive in the host (Galan et al., supra).

The vector was then modified to include a BamHI-EcoRI-BamHI* adaptor inserted into the single BamHI site of the plasmid (FIG. 1). The insert was designed so that the downstream BamHI site was altered to preserve only one BamHI site. The EcoRI site at the downstream end of the LT-B gene was in the same reading frame as the EcoRI site in the β-galactosidase gene of lambda gt11. Termination codons occurred downstream in all three reading frames. The Bam-Eco-Bam adaptor was inserted into the BamHI site as indicated in FIG. 1 and transformed into *E. coil* X6097 cells. Fifteen transformants were pooled together and grown overnight in 10 ml of LB (Luria-Bertani) medium. The plasmids were isolated by the miniprep method and, to remove excess copies of the adaptor after the initial ligation, the resulting plasmids were digested with EcoRI and resolved in a soft agarose gel. The plasmids were recircularized and transformed again into X6097. Ten transformants were picked, their plasmid DNA isolated, and the orientation and copy number of the insert was confirmed by sequencing. Only one colony had the adaptor in the correct orientation (some had it in the opposite orientation, others had multiple copies of the adaptor and in different orientations). The new construct retains one BamHI site and inserts an EcoRI site in the same reading frame as the EcoRI site in lambda gt11. A new termination codon (TAA) is also inserted so, that terminators occur in all three reading frames immediately downstream from the EcoRI site.

A positive clone designated G11 from the *C. jejuni* library constructed in the phage expression vector lambda gt11 was isolated. Western blot analyses were carried out using anti-serum raised in rabbits against *C. jejuni*, and anti-β-galactosidase antiserum (Promega Biotec, Madison, Wis.). A single band was detected with each antiserum corresponding to a fusion protein of an apparent total molecular weight of 163 kd. Beta-galactosidase protein has a molecular weight of 114 kd; thus the inserted DNA fragment encodes a product of 49 kd. The molecular weight of the complete *C. jejuni* flagellin is 63 kd (Nuitjen et al., 1990, supra). Two μgs of the recombinant phage DNA were digested with EcoRI, yielding two small DNA fragments in addition to the large lambda phage DNA arms. These two fragments corresponded to approximately 0.8 kb (designated U band) and 0.3 kb (L band) as judged by their electrophoretic mobility in a 1% agarose gel.

The plasmid pBEB was digested with EcoRI, dephosphorylated, and isolated from a soft agarose gel. The U band was ligated to pBEB, and X6097 *E coli* cells were transformed with the ligation mixture. Five colonies were isolated, their plasmid DNA extracted and digested with EcoRI to check for the presence of the insert. Next, the plasmids were sequenced using the ABI automated DNA sequencer 373A. One colony had plasmid with the insert in the correct orientation, and it was call pBFU.

The LT-B/fla fusion gene was under constitutive expression in X6097. The fusion protein was detected at several growth times. The best recovery, i.e. the greatest yield of the fusion protein relative to the total protein, was when cell density corresponding to $OD_{600}$ of about 0.8 was reached. The fusion protein was detected by Coomassie staining, and Western blot analyses using chicken anti-flagellin serum (FIG. 2), rabbit anti-*C. jejuni* serum, affinity purified rabbit anti-*C. jejuni* flagellin antibodies and rabbit anti-LT serum (FIG. 2). The fusion protein was not recognized by a monoclonal antibody directed against the 63 kd flagellin protein, presumably because the monoclonal antibody is directed against an epitope not present in our fusion protein since only 46% of the flaA gene is expressed. The fusion protein has a MW of 43 kd (16 for LT-B and 27 kd for the U band). The protein could not be detected from the pBEB transformed X6097 control. The LT-B/fla, fusin gene DNA sequence is presented in FIG. 3.

Since highly expressed proteins are often stored in inclusion bodies, the inclusion bodies of pBFU were isolated. The fusion protein was 10 to 15 times enriched compared to total cell lysis as judged by Coomassie staining. The fusion protein from the inclusion bodies was not solubilized in solution containing 4M urea. The fusion protein made up 10% of the total protein in the inclusion body lysate as judged (by visual comparison) by Coomassie staining.

The inserted adaptor contained an EcoRI site that was used to insert the U band. In addition, it contained a stop codon (TAA) in the third reading frame not present in the pYA3081 vector. The expression in the vector was constitutive. The fusion protein was detected as predicted. It is possible that a sequence that is inhibitory to the *E. coli* machinery was not present in the U sequence. Like most foreign overexpressed proteins, the fusion protein was stored in inclusion bodies that could be readily isolated. Another version of the LT-B vector (pYA3047) has been described (Jagusztyn-Krynicka et al., supra) that has the leader sequence of the protein, and hence would likely produce a protein that is secreted into the medium. The vector has the same MCS at the 3' end of the LT-B gene as pYA3081, but there are two EcoRI sites in the leader sequence area. Therefore, a fragment from lambda gt11 could be first subcloned into pBEB as described herein, and then directionally subcloned into pYA3047 using the restriction sites at the ends of the MCS.

The novel protein is useful for the prevention of infection and colonization of chickens by Campylobacter spp. After harvesting from cultures, the protein may be extracted with detergent, precipitated with urea and dialyzed against 0.01M Tris buffer. The semi-purified soluble portion may be administered to chickens in water wih 0.25M sodium bicarbonate, 1.0 mg total protein/ml, 1 ml/bird. In one experiment, fifty chickens were given the fusion protein vaccine and challenged to an excess of *C. jejuni* at 3 weeks of age. Fifty control birds were only challenged. At 5 weeks of age, the birds were sampled for presence and number of *C. jejuni*. The number of individual birds colonized at the sampling time was 49% for the controls and 24% for the vaccinates. The number of organisms per bird was $10^{1.62}$ for the control birds and $10^{0.89}$ for the vaccinates.

The following examples are intended only to further illustrate the invention and are not intended to limit the scope of the invention as defined by the claims.

EXAMPLES

Example 1

Construction of pBEB

Plasmid pYA3081 was propagated in *E. coil* X6097. Plasmids were isolated with the Magic Minipreps DNA purification system (Promega). After restriction enzyme digestion, plasmids to be ligated to insert DNA were dephosphorylated with calf intestinal phosphatase (Promega). All ligation reactions were done using T4 DNA ligase (Promega).

Oligomers used to create the BamEcoBam* adaptor were as follows:

1) BAMECOF=: 5'-GAT CCT GAA TTC GCT AAT-3' (SEQ ID NO:3)
2) BAMECOREV=: 3'-GAC TTA AGC GAT TAC TAG-5' (SEQ ID NO:4)

The oligomers were annealed to form the adaptor and then phosphorylated with T-4 kinase (GIBCO BRL). New constructs were transformed into *E. coil* by electroporation. Insert orientation was confirmed by sequencing using the Taq DyeDeoxy Terminator Cycle Sequencing Kit (ABI) with primers and oligomers synthesized at the UGA Molecular Genetics Core Laboratory on an ABI oligonucleotide synthesizer. The sequencing primers were designed based on the published LT-B (Clements, supra) sequences.

Example 2

Construction of *C. jejuni* genomic library

A *C. jejuni* genomic library was constructed in the phage vector lambda gt11 by the method of Young (1985. *PNAS,* vol. 82, pp. 2538–2587, and herein incorporated by reference) with a commercially available kit (Promega) and plated on *E. coil* Y1090. Plaque blots were initially screened with rabbit antiserum against total outer membrane proteins of *C. jejuni*. After two rounds of plaque purification, a plaque was selected that reacted with antibody affinity purified to *C. jejuni* flagellin. The phage DNA was extracted and digested with EcoRI (Promega), resolved in a 1% soft agarose gel (NuSieve GTG Agarose, FMC), and then extracted from the agarose with phenol. A 0.8 kb fragment of *C. jejuni* DNA was inserted into pBEB which was then transformed into *E. coil* X6097. Plasmid pBEB is illustrated in FIG. 1.

Example 3

Detection of the Fusion Protein in X6097 cells

One colony of interest was grown overnight (ON) in 10 ml LB medium. The following day, 5 ml of LB was inoculated with 50 μl of the ON cultures. At various times during incubation (i.e. 1, 2, 3 and 4 h), 1 ml of the cultures was transferred to a microfuge tube, centrifuged at 12,000 g for 1 min, and the cell pellet was saved at −20° C. At each sample collection, the OD of the cultures were checked at 600 nm. After the 4 h incubation time, the cell pellets were resuspended in 10 μl of 2× sample buffer, and the samples were run on SDS-PAGE (4.5% stacking gel and 10% resolving gel). Two gels were run, one for total protein with Coomassie blue or with a silver stain and the other for Western blot analysis.

Western blot analyses were performed as described by Towbin et al (1979. *PNAS*, vol. 76, pp. 4350–4354). Blots were treated with a 1:200 dilution of chicken anti-*C. jejuni* serum or rabbit anti-LT before adding the secondary antibody (goat-anti rabbit IgG alkaline phosphatase conjugate, Bio-Rad), and developed with the substrate solution (5-bromo-4-chloro-3-indolyl phosphate/nitro blue tetrazolium) as described by Sambrook et al. (1989. In *Molecular Cloning, A Laboratory Manual,* Cold Spring Harbor, N.Y.: Cold Spring Harbor Laboratory). Results are shown in FIG. 2.

We claim:

1. A recombinant fusion gene consisting of the sequence of FIG. 3 (SEQ ID NO: 5).

2. A plasmid comprising the fusion gene of claim 1.

* * * * *